United States Patent [19]

Linner et al.

[11] Patent Number: 4,707,998

[45] Date of Patent: Nov. 24, 1987

[54] APPARATUS AND METHOD FOR ULTRARAPID COOLING OF BIOLOGICAL SAMPLES

[75] Inventors: John G. Linner; Stephen Livesey, both of The Woodlands, Tex.

[73] Assignee: The Board of Regents, The University of Texas, Austin, Tex.

[21] Appl. No.: 939,701

[22] Filed: Dec. 3, 1986

[51] Int. Cl.$^4$ .......................... F25C 5/08; F26B 13/30
[52] U.S. Cl. .................................... 62/349; 118/50.1; 34/92; 62/100; 62/55.5; 422/131
[58] Field of Search ...................... 62/55.5, 514 R, 78, 62/265, 266, 268, 100, 62, 275, 349, 340; 34/92; 118/50, 50.1; 424/3, 4; 422/131

[56] References Cited

PUBLICATIONS

Escaig, Jacques, "New Instruments which Facilitate Rapid Freezing at 83K and 6K", *Journal of Microscopy*, Jun. 1982, at pp. 221–229.
Boyne, Alan F., "A Gentle, Bounce-Free Assembly for Quick-Freezing Tissues for Electron Microscopy: Application to Isolated Torpedine Ray Electrocyte Stacks", *Journal of Neuroscience Methods*, 1 (1979), pp. 353–364.
Coulter, H. David, "Freezing and Drying of Biological Tissues with a Toggle-Link Helium Freezer and an Improved Freeze-Drying Apparatus: Application to Neuropeptide Immunocytochemistry", *Journal of Electron Microscopy Technique*, 4 (1986), at pp. 315–328.
Reichert-Jung, "Cryovacublock"—Instruction Manual.
Escaig, Jacques, "Control of Different Parameters for Optimal Freezing Conditions", *Science of Biological Specimen Preparation*, pp. 117–122.
Handley, Dean A., et al., "The Design and Use of a Simple Device for Rapid Quench-Freezing of Biological Samples", *Journal of Microscopy*, Mar. 1981, at pp. 273–282.
Polaron Instruments Inc., "The Slammer" (brochure).
Med-Vac Inc., "Cryopress" (brochure).
Reichert-Jung, "Cryofract 190 Cryoblock" (brochure).
Quick Freezing Devices, "Quick Freezing by Bounce-Free Delivery" (brochure).
Moor, H. et al., "The Influence of High Pressure Freezing on Mammalian Nerve Tissue", *Cell and Tissue Research*, (1980), at pp. 201–216.

*Primary Examiner*—Henry A. Bennet
*Attorney, Agent, or Firm*—Arnold, White & Durkee

[57] ABSTRACT

A method and apparatus for ultrarapid cooling of tissue samples against a chilled cryogenic surface. The cryogenic surface is enclosed in an ultra-high hydrocarbon free vacuum chamber during cooling of the cryogenic surface by a helium cryopump or multiple-stage refrigerator. Dry helium gas is introduced from an external source to raise the chamber pressure just prior to slamming or plunging a sample against the cryogenic surface. The cryogenic surface is heated for regeneration or cleaning purposes between each successive sample. During heating and cleaning of the cryogenic surface, an evacuated thermal break functionally separates the surface from the helium cryopump or multiple-stage refrigerator used to cool the surface. After regeneration or cleaning the cryogenic surfce, dry helium gas is reintroduced into the thermal break from an external source, thereby enabling the helium cryopump or multiple-stage refrigerator to rapidly recool the cryogenic surface and repeat the cycle for sequential samples with minimal regeneration time between each sample.

33 Claims, 4 Drawing Figures

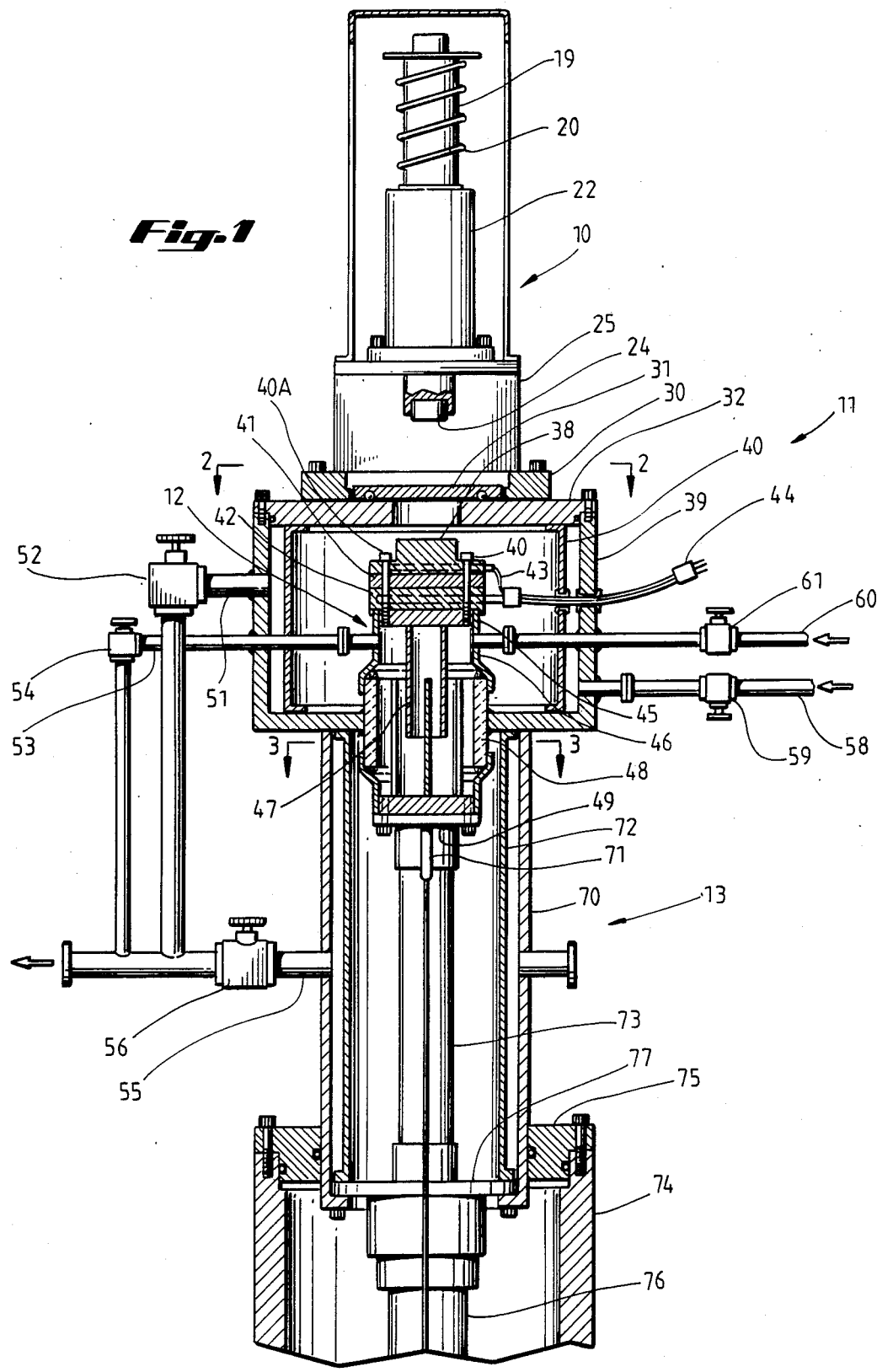

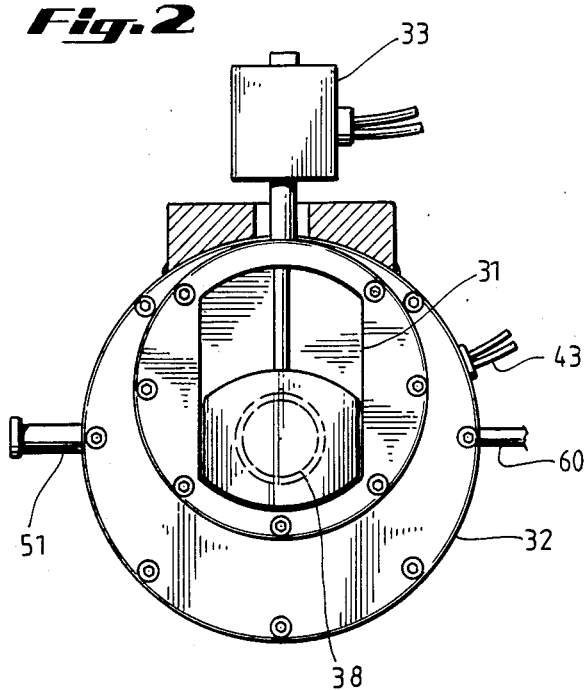
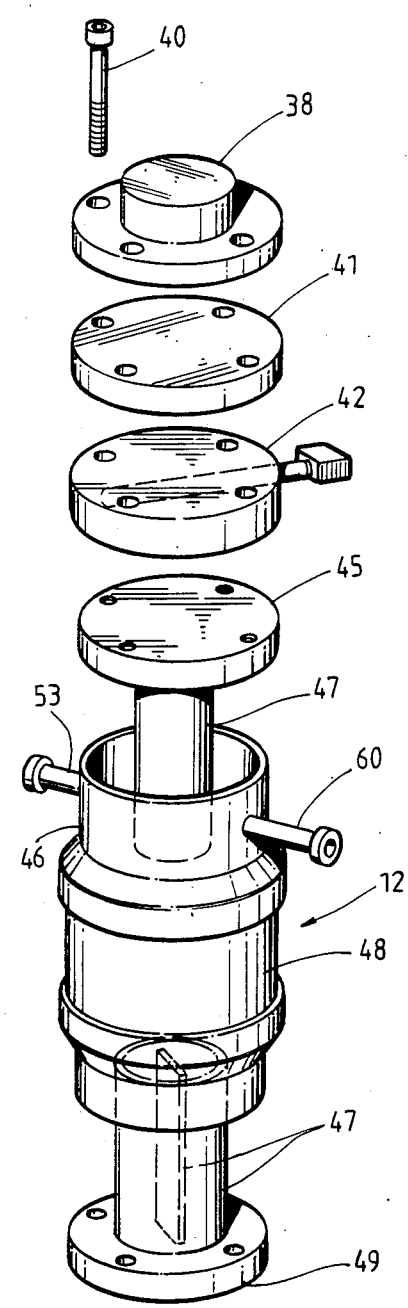
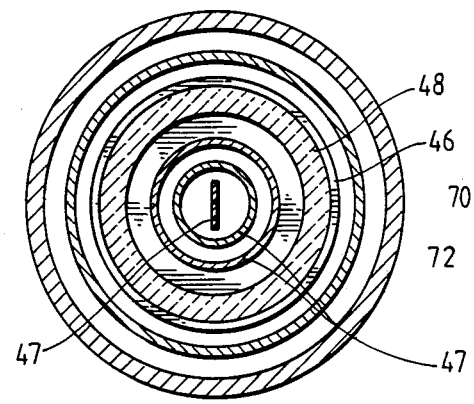

APPARATUS AND METHOD FOR ULTRARAPID COOLING OF BIOLOGICAL SAMPLES

BACKGROUND OF THE INVENTION

1. Field of the Invention

This invention relates to apparatus and method for the ultrarapid cooling of biological samples. Ultrarapid cooling is a preparatory step to the cryopreparation of biological samples in apparatus such as that described in commonly assigned U.S. Pat. Nos. 4,510,169 and 4,567,847 issued to John G. Linner and commonly referred to as "The Linner Process" or "The Linner Apparatus". It is well known in the medical arts that to examine biological samples and determine the cellular structure, and function thereof, the samples must be "fixed" with minimal alteration of ultrastructural integrity prior to the application of nearly all analytical methodologies. The apparatus of this invention can be used to ultrarapidly cool biological samples without the formation of resolvable ice crystals so that the ultrastructural integrity of the sample is not altered.

The terms "biological samples", "tissue samples", and "biological tissue" are used throughout this disclosure to refer to samples that can be ultrarapidly cooled by the method and apparatus of this invention. The terms are used interchangeably and are not intended as a limitation on the functional capability of the method or apparatus disclosed herein. The terms should be understood to include small tissue samples appropriate for microscopic examination and larger tissue masses such as corneas which are appropriate for transplantation The terms should be understood to include any material composed of one or more cells, either individual or in complex with any matrix or in association with any chemical; and to include any biological or organic material and any cellular subportion, product or by-product thereof. The terms should be further understood to include without limitation sperm, eggs, embryos, blood components and other cellular components. The contemplated utility of the apparatus of this invention is not limited to specific types or sizes of tissue, rather it should be understood to refer to any tissue made up from cells. The apparatus of this invention can be designed or adapted to any size, shape or type of cellular tissue. Therefore, the terms "tissue" and "tissue samples" are used interchangeably and are not limiting on the uses to which the method and apparatus of this invention can be placed.

Although the method and apparatus of this invention are preferably used as a preliminary step in the cryopreparation of biological samples for ultrastructural analysis, i.e. electron microscopy, it should be understood that this is not intended as a limitation on the utility of the apparatus and method of this invention. To the contrary, the ultrarapid cooling method and apparatus of this invention have demonstrated utility in any area in which the ultrastructure of cellular components is desirably maintained in an unaltered state. Examples of such utility include, but are not limited to, electron microscopy, tissue preservation, tissue and organ transplants and various analytical and diagnostic methodologies. Therefore, although the method and apparatus of this invention are typically described in relationship to electron microscopy this should be understood not to be a limiting factor on the utility of the invention.

Although the examination of tissue by use of various microscopes or related magnifying apparatus has been practiced for many years, there has been an inherent problem in preparing tissue for use with contemporary high resolution analytical microscopes, such as the STEM electron microscopes, which permit the examination of sample constituents via X-ray analysis at powers of from 500X to 500,000X with point to point resolution of 2 to 3 Angstrom units.

It is difficult to interpret the results of tissue analysis while concomitantly assessing the extent of various artifacts produced during the tissue preparation processes. It is thus essential that artifacts be avoided wherever possible. The term "artifact" refers to a product of artificial character due to extraneous agency. Another problem results from physical shrinkage of the tissue sample itself, which results in alteration of ultrastructure and massive rearrangement of infrastructural resolution.

During the so-called "Golden Age of Morphology" the predominant underlying goal in qualitative and quantitative microscopy has been an aesthetically pleasing image. This goal is readily attainable with the fixation methods and apparatus which are currently available. However, it has become essential that the aesthetically pleasing image, which is produced by the preparation process, also yield a tissue sample which accurately reflects the true condition of tissue in the living organism, i.e., approaching the "living state." This is the problem which is addressed and solved by The Linner Apparatus and Process. One essential step in the preparation process is the cryopreparation or cryofixation procedure (as opposed to the freezing procedure). The cryopreparation method and apparatus of this invention results in the preparation of tissue samples which are readily usable in known magnification and analytical apparatus.

In currently known cryopreparation and freeze-drying devices and methods, problems and limitations are encountered in attempts to rapidly cool the tissue sample without physically harming the sample. If the temperature decrease in the sample to its full depth does not take place at a sufficiently rapid rate, artifacts appear, the ultrastructural integrity of the sample may be damaged and the sample will not appear in its "living state." The prior art has therefore attempted to achieve a rapid rate of temperature decrease to the full depth of the sample, in order to minimize such damage.

Although the primary thrust of this application is in the preparation of tissue samples for analysis by current magnification apparatus, the invention is not intended to be so limited. More specifically, the "preparation" of tissue should be understood to refer to preparation of tissue for analysis as well as the cryofixation of tissue in anticipation of transplantation, modification, in vitro or in vivo cellular growth, fertilization, animated suspension or the more typical resin impregnation, setting, infiltration and analysis. The apparatus of this invention can be used to prepare tissue for any medical or analytical procedure without the ultrastructural damage previously thought to be inevitable in cryopreparation.

The apparatus of this invention is to be distinguished from contemporary freeze-drying apparatus. Freeze-drying is a technique which is well known in the art together with the equipment necessary to implement such freeze-drying. See, for example, U.S. Pat. No. 4,232,453. Although in certain freeze-drying techniques liquid nitrogen is used as a cooling medium, the tissue or sample itself does not attain such temperature. Freeze-drying normally contemplates sample temperatures of −50° C. to −80° C. In contrast, the ultrarapid cooling step of the cryopreparation process of the Linner Process and Apparatus contemplate sample temperatures of −196° C. or less. Therefore, for purposes of this application the terms "cryopreparation" and "cryofixation" are used in distinction to conventional "freeze-drying" technology (−50° C. to −80° C.).

2. Description of the Related Art

The most common prior art method for preparation of tissue samples for analysis is by means of chemical fixation and organic solvent dehydration. Inherent in prior art processes is the concomitant artifact creation, sample shrinkage and resultant damage to and modification of tissue characteristics. These tissue characteristic modifications, whether in the form of artifacts or the like, require interpretation by the individual or apparatus analyzing or evaluating the sample. This introduces, in many instances, an unsatisfactory risk of error.

Chemical fixation is a well known technique and has served the analytical biologist well for many years and undoubtedly will continue to do so in certain limited applications. However, as the use of tissue sample analysis becomes more complex and the use of such analysis becomes more widespread, alternatives to chemical fixation are demanded. This is especially true as advances are being made in the magnification and analytical apparatus which are available. It is necessary that tissue preparation methods and the apparatus necessary to prepare tissue samples be equally advanced as the analytical tools, i.e., electron microscopes, which are being used to analyze the samples. Obviously, if the technology for tissue sample preparation is behind the technology of microscopy then the advanced microscopes cannot be used to full advantage by the morphologist or other tissue examiner.

Similarly, it is essential that cryopreparation methods and apparatus develop concurrently with other medical technology, i.e., surgical transplant techniques, bioengineering and biogenetics. In short, cryopreparation is an essential intermediate step in evolving processes using or analyzing cells or tissue. If cryopreparation apparatus does not evolve then the thrust of medical technology into unexplained and unexplored medical arts will be blunted. The apparatus of this invention represents the cryopreparation breakthrough that will permit research into the use and preparation of biological tissue to keep pace with other advances in medical technology. The ultrarapid cooling apparatus of this invention provides the mechanism for eliminating the problems associated with available cryofixation apparatus.

The most common alternative to chemical fixation and organic solvent dehydration is freeze-drying cryofixed samples. Freeze-drying following cryofixation is a well documented and well known technique for tissue preservation. It has several advantages. Freeze-drying results in a near-instantaneous arrest of cellular metabolism. There is also a stabilization and retention of soluble cell constituents through elimination of solvent contact with the sample. These are significant advantages to cryofixation freeze-drying that have resulted in a great deal of research in attempting to apply cryofixation and freeze-drying techniques to known tissue preparation processes.

Unfortunately, freeze-drying technology inherently possesses a number of disadvantages relevant to tissue preparation methodologies. The primary disadvantage in currently available freeze-drying techniques and apparatus is the inherent formation of ice crystals. As can be readily appreciated, the formation of ice crystals destroys the ultrastructural integrity of the tissue sample being reviewed. The image is distorted and the cytoplasm becomes reticulated. The formation of ice crystals in the sample can also result in a change in pH within microcompartments of the tissue (eutectic formation) which possibly can result in abnormal tertiary conformation of macromolecules. There is also the possibility that proteins will denature and precipitate. These are but a few of the disadvantages which are inherent in the freeze-drying process.

This general topic is discussed in some detail together with other prior art methods in an article entitled "Freezing and Drying of Biological Tissues for Electron Microscopy", Louis Terracio and Karl G. Schwabe, published in *The Journal of Histochemistry and Cytochemistry*, Volume 29, No. 9 at pp. 1021–1028 (1981). Problems associated with artifact formation are described in "Understanding the Artefact Problem in Freeze-Fracture Replication: A Review", *The Royal Microscopial Society,* (1982) at pp. 103–123.

A general principle found applicable to freezing techniques, which has demonstrated utility in the preparation of tissue samples, is that as the cooling rate increases, tissue fluids can be "vitrified" without the separation of water to extracellular spaces. The term "vitrified+" or "vitrification" refers to the cryopreparation of tissue samples without the formation of resolvable ice crystals within the cellular structure. It has been postulated that regardless of the rate of cooling, ice crystals may still be formed, but as the cooling rates increase the size of the intracellular ice crystals decreases. The small size or absence of ice crystals at high freeze rates is of course a substantial advantage in morphology retention as this results in minimal artifact creation and minimal ultrastructural alteration or damage during tissue dehydration. The apparatus of this invention provides the ultrarapid cooling of tissue samples to the vitreous phase in less than one second. The ultrarapid cooling according to the present invention is followed by dehydration of the tissue sample while in the state of reduced partial pressure of water vapor without substantial ultrastructural damage to the tissue cells.

Historically, the criteria by which the techniques for rapid supercooling have been judged was not the cooling rate of the system but simply the temperature of the environment in which the tissue was frozen. Thus, the term rapid supercooling has been applied to any system in which the supercooling agent has a temperature of −150° C. or below. The effectiveness of a cooling system, however, is dependent upon the rate at which heat is removed from the sample. Heat transfer is dependent not only on the temperature of the freezing system but also on its physical and thermal characteristics, as well as the size and thermal characteristics of the tissue.

The most commonly used technique for rapid supercooling is to immerse or "quench" the sample in a fluid cooling bath. The most commonly used fluids for quenching are liquid nitrogen, isopentane, propane and fluorocarbons such as Freon 12 and Freon 22. Although liquid nitrogen is generally regarded as an ideal quenching fluid due to its low temperature (−196° C.), there are inherent disadvantages in the use of liquid nitrogen due to the occurrence of tissue surface film boiling caused at least in part by the low heat of vaporization of liquid nitrogen. Film boiling is a characteristic of liquid nitrogen that inhibits the heat transfer rate by actually insulating the sample.

An alternative method for rapid supercooling is applying the tissue sample to the polished surface of a cryogenic surface such as a chilled metal block. This typically involves opposing the tissue sample to a polished flat metal surface by pressing it firmly against the surface of the metal. Silver and copper are typically used as the polished metal blocks. This method is designed to take advantage of the high thermal conductivities and heat capacities of these metals when cooled to liquid nitrogen or liquid helium temperatures. The critical step in chilling on the surface of a metal is making firm contact with the dry, chilled metal surface with no rotational, translational or rebounding motion. Certain commercially available apparatus having known utility in the medical arts address and provide "bounce-free" freezing. Credit for the development of this apparatus is generally accorded to Dr. Alan Boyne of the University of Maryland School of Medicine.

The Boyne apparatus and method included one or more copper bars partially submerged in a container filled with liquid nitrogen at $-196°$ C. The end of the copper bar was a mirror-finished smooth cryogenic surface, and the thermal conductivity of copper enabled the surface to be maintained at about $-196°$ C. Cold nitrogen gas from vaporization of the liquid nitrogen, which escaped past the end of the copper bar, helped to reduce the contaminants on the cryogenic surface. A tissue sample was then dropped by gravity against the surface. To reduce the bounce of the sample against the surface, the Boyne sample delivery assembly employed a weight dampening system utilizing glycerol to absorb the impact. Each copper bar must be cleaned after slamming a sample. The drawbacks of the Boyne apparatus included problems of hydrocarbon contamination and condensation on the cryogenic surface, inability to eliminate all bounce or vibration between the sample and surface, undesirable precooling of the sample with escaping nitrogen gas, and delays for cleaning and regenerating the cryogenic surface of the copper bars between each sequential sample. The Boyne method and apparatus thus could not reliably provide tissue samples with good ice crystal-free zones nor was it capable of properly vitrifying the samples beyond a depth of 10 to 15 microns.

Further development of freezing tissue samples against a metal block has been credited to Jacques Escaig of Paris, France. The method and apparatus of Escaig is described in "Control of Different Parameters For Optimal Freezing Conditions", Jacques Escaig, published in *Science of Biological Specimen Preparation*, at pp. 117-122 (1984). The Escaig apparatus also is disclosed in Swiss Patent No. 614,532, French Patent No. 2,337,878 and German Patent No. 2,700,196. Escaig provided several significant features not shown in earlier methods or devices for vitrifying tissue against a metal block. The Escaig method and apparatus cool a copper block with liquid helium, rather than liquid nitrogen, in order to increase the cooling rate of a tissue sample or specimen. Escaig disclosed that the average thickness of ice crystal-free zones in the tissue sample were much larger when the copper block was cooled by liquid helium rather than liquid nitrogen. Additionally, Escaig pointed out that the factors influencing the freezing process, independent of the tissue sample itself, are thermal contact between the specimen and metal block, condition of the block surface, specimen slipping, sample holder bounce and sample holder contact strength. Escaig obtained some control of these factors by utilizing a vacuum pump to keep the metal block under vacuum of $1 \times 10^{-3}$ Torr. until just before slamming the specimen against the block, in order to reduce contamination on the block surface. Escaig also utilized an electromagnet to bring the specimen in contact with the block in order to improve mechanical contact between the specimen and the block.

According to the Escaig apparatus and method, a copper block is enclosed in a vacuum chamber. The chamber is then evacuated to approximately $1 \times 10^{-3}$ Mbar with an external vacuum pump system. After a vacuum is reached in the chamber, Escaig employed an external nonreusable cryogen source—liquid helium pumped from a reservoir—to cool the copper block. The liquid helium is transmitted to a passage adjacent to the block through a conduit in the vacuum chamber. When the block is cooled to the desired temperature, Escaig used an electropneumatic system to open a stem insert in the liquid helium passage for releasing cold helium gas for several seconds into the vacuum chamber itself. The cold helium gas admitted into the vacuum chamber is obtained from vaporization of the liquid helium which was used to cool the metal block. The cold helium gas raises the pressure inside the vacuum chamber. When atmospheric pressure is reached inside the vacuum chamber, a shutter providing access to the vacuum chamber is spring biased to open the chamber and activiate downward movement of a sample delivery assembly, which plunges or slams the tissue sample through the shutter opening and against the block. Opening of the shutter also triggers closing of the stem insert to stop the release of cold helium gas into the chamber.

Several problems have been encountered in the Escaig apparatus. Because Escaig used cold helium gas to bring the vacuum chamber up to atmospheric pressure, a tissue sample precools for approximately 15 milliseconds as it descends through a layer of cold helium gas at atmospheric pressure prior to plunging or slamming against the metal block. The precooling effect of the Escaig device is undesirable due to unwanted effects, such as ice crystal formation, on the physiology of the tissue sample. Additionally, movement of liquid helium and helium gas through the vacuum chamber inevitably resulted in vibration of the metal block, which was undesirable because it reduced or prevented good mechanical contact between the specimen and block. Escaig's use of nonreusable liquid helium to cool the block further has proved to be expensive, somewhat unsafe and cumbersome due to the necessity of recooling the entire liquid helium system between each tissue sample. The end result was extremely slow turnover time for regenerating the copper block between each sample. Additionally, cleaning the block in the Escaig apparatus proved difficult because of condensation on the block forming after a sample was slammed against the block. To remove the condensation, pressurized nitrogen gas and hot air could be applied against the block. However, removal of the block for repolishing or other cleaning required disassembly of the vacuum chamber itself. Even if the block was not removed, the problems in regenerating the block surface resulted in turnover time between samples which is commercially unacceptable. It was therefore not possible to use the Escaig device if a large number of sequential samples was desired.

The cryopreparation apparatus and method according to the present invention solves the problems inherent in the prior art including the Escaig apparatus and method. The present invention addresses the problems in the prior art of slow turnover time between the vitrification of tissue samples, by enabling several samples to be vitrified sequentially. The present invention also solves the problems in the prior art caused by use of nonreusable liquid helium or other coolant, undesirable precooling of the tissue sample before contact with the cryogenic surface, cleaning and reheating the cryogenic surface between each sample, and removal of the cryogenic surface from the apparatus.

SUMMARY OF THE INVENTION

The apparatus and method of the present invention provide for ultrarapid cooling or vitrification of tissue samples by slamming or plunging the samples against a chilled cryogenic surface. The apparatus contemplates chilling of the tissue sample against a mirror-finished smooth cryogenic surface. The cryogenic surface is enclosed in an ultra-high, hydrocarbon free vacuum chamber. In the preferred embodiment, introduction of noncondensable dry helium gas at room temperature into the chamber just prior to plunging or slamming the sample enables the chamber pressure to be raised and a shutter providing access into the chamber to be opened without undesirable condensation on the cryogenic surface, or dehydration and precooling of the tissue sample during its downward movement through the shutter opening towards the cryogenic surface. An external dry helium source is used to supply dry helium to the chamber.

In the preferred embodiment, rapid regeneration of the cryogenic surface between successive samples is enabled by the use of a thermal break and a heating unit proximate to the surface. The thermal break is positioned generally between the cryogenic surface and a helium cryopump or multiple-stage refrigerator. The thermal break, when evacuated, controllably separates the cooling of the helium cryopump from the cryogenic surface. A heating unit is electrically activated to heat the cryogenic surface for cleaning and removing condensation between tissue samples, while the thermal break is evacuated. Before a sample is slammed against the cryogenic surface, dry helium gas is introduced into the thermal break, and the cryogenic surface is rapidly re-cooled to the desired temperature, preferably between $-270°$ C. and $-200°$ C. Thus, the present invention enables sequential vitrification of tissue samples against the cryogenic surface without delays for regeneration and recooling inherent in the prior art. The present invention also provides a cryogen-independent recirculating refrigerant cycle for cooling the cryogenic surface rather than an external cryogen source such as liquid nitrogen or liquid hydrogen as used in the prior art.

Another advantage of the apparatus of this invention is the ability to cryoprepare tissue without overt disruption or destruction of the morphological characteristics of the ultrastructure of tissue cells. The cryopreparation method and apparatus of the present invention provide for ultrarapid cooling of tissue samples so that the tissue then may be dehydrated while maintained in the solid, vitreous phase without creating unnecessary artifacts which restrict interpretation by conventional analytical apparatus.

The cryopreparation process of the present invention has demonstrated an extraordinary application in the transplanting of corneal tissue. Prior to this invention attempts to transplant corneas which involved a necessary freezing or freeze-drying of the corneas after removal from the donor invariably resulted in a clouded cornea upon transplanting. The clouding remained for from as little as several days to the life of the transplanted cornea. This physical condition of the transplanted cornea was caused by ice crystal formation in the cornea itself and concomitant damage to the stroma. Use of the apparatus of this invention has enabled ophthalmologists to cryoprepare corneas and to then transplant those corneas to recipients with virtually negligible clouding or crystal formation. The ability to so transplant corneas represents an exceptional advantage to the process of this invention as well as a medical breakthrough in corneal transplant surgery.

DESCRIPTION OF THE DRAWING

FIG. 1 is a side view, partially in section, of the preferred embodiment of the present invention.

FIG. 2 is a cross-sectional view of the preferred embodiment of the present invention, taken along section line 2—2 of FIG. 1.

FIG. 3 is a cross-sectional view of the preferred embodiment of the present invention, taken along section line 3—3 of FIG. 1.

FIG. 4 is an exploded perspective view of the thermal break as used in the preferred embodiment of the present invention.

DETAILED DESCRIPTION OF THE PREFERRED EMBODIMENT

In the apparatus of this invention it is a fundamental prerequisite that the desired tissue is obtained. Tissue samples are collected by a variety of means, i.e., surgical extraction, withdrawn blood samples, binders and any of a variety of other techniques which are well known and conventional. The particular method of obtaining the biological sample is not limiting on the apparatus of this invention. However, the preparation of the tissue sample in the apparatus of this invention is enhanced if the tissue sample is processed as soon after excising as is possible.

The preparation of the tissue sample takes place immediately as it is received. The tissue sample cannot be retained in a fixative, i.e., formaldehyde, or another biologically active stabilizing solution, in an attempt to maintain the sample during shipping, storage or other necessary operations. It is also critical that the sample not be routinely frozen or otherwise physically modified prior to preparation according to the method of this invention. The sample may later be physically sectioned or otherwise physically prepared for long-term storage in apparatus or use with various currently available commercial analytical apparatus.

In one application of this invention a tissue sample is prepared for analysis. The preferred optimum biological sample for preparation in the apparatus of this invention is a fresh one cubic millimeter biopsy sample. This sample must be vitrified as soon as possible. By vitrifying or vitrification it is intended to make reference to a process which results in cryofixation of the sample which is different from "frozen." In the process of vitrifying, the cooling apparatus which is used renders the sample in the vitreous phase such that soluble and insoluble moities contained in the tissue sample are not disturbed, translated, or altered nor are they concentrated (as eutectics). By definition, a vitrified liquid will shatter when undergoing a shear stress, e.g., window glass. The vitreous phase involves the conversion of liquid water into an amorphous or "glass" phase. This is accomplished by rapidly supercooling the tissue sample by opposing it "bounce-free" onto the highly polished (mirror-like) condensate-free cryogenic surface preferably at between −270° C. and −200° C. It is preferred that such rapid supercooling be completed in less than one second.

Depending on the anticipated time lag between supercooling of the sample and dehydration of the sample, the sample may be stored submerged in a liquid nitrogen dewar at −196° C. Once the sample has been dried and embedded properly it may be stored virtually indefinitely without cytoplasmic reticulation or other forms of cellular catabolism which will cause modifications and crystal lattice transitions resulting in undesirable artifacts which render the tissue uninterpretable as analytical data.

In the preferred embodiment of the present invention, the major components of the cryopreparation apparatus include sample delivery assembly 10, upper vacuum chamber 11, lower vacuum chamber 13, thermal break 12, and cryogenic surface 38. Cryogenic surface 38 is enclosed within upper vacuum chamber 11, and preferably may be easily removed from the chamber for replacement, reconditioning, or repolishing of the surface. In the preferred embodiment, thermal break 12 is positioned generally between upper vacuum chamber 11 and lower vacuum chamber 13. It should be understood, however, that the thermal break may be positioned in any manner for controllably separating the cryogenic surface from the cooling of a helium cryopump or multiple-stage refrigerator. The chambers are evacuated to reach a hydrocarbon free vacuum and cooled to the desired temperature with the cryogenic surface cooled to preferably between −270° C. and −200° C. One or more tissue samples are then slammed or plunged against the cryogenic surface 38. The cryogenic surface is then cleaned and heated to room temperature while lower vacuum chamber 13 is maintained at the desired cool temperature. The thermal break establishes an insulating region between the cryogenic surface and the helium cryopump or multiple stage regrigerator cooling the lower vacuum chamber. After the cryogenic surface is cleaned, the thermal break is refilled with dry helium gas under pressure, facilitating rapid recooling of the cryogenic surface to between −270° C. and −200° C.

Sample delivery assembly 10 comprises plunger 19 provided with bias means shown as spring 20 extending from within plunger housing 22. Plunger 19 is cooperatively aligned and moveable into and out of housing 22. The spring or bias means serves to recoil the plunger from cryogenic surface 38 after a specimen or tissue sample is plunged against the cryogenic surface. The plunger 19 is further provided with a magnetic sample holder 24. Sample holder 24 includes a magnetic disk to improve mechanical contact between the specimen and the cryogenic surface, and includes mounting means for the tissue sample. Sample holder 24 further includes elastic material such as a foam rubber cushion or other suitable compressible and resilient material to insure that the specimen or tissue sample, when mounted on the sample holder and plunged against the cryogenic surface, will avoid undesirable specimen compression and deformation. The sample delivery assembly 10 further includes support structure 25 cooperatively engaged to plunger housing 22 to position the assembly directly above upper vacuum chamber 11. The plunger 19 is electromagnetically or electropneumatically actuated to move the tissue sample downward against the cryogenic surface when shutter 31 is opened. Other means for actuating the plunger 19, however, are contemplated within this invention.

Upper vacuum chamber 11 is provided with upper end plate 32 and side walls 39, and is preferably composed of stainless steel and constructed so that it may be vacuum sealed. Shutter 31, preferably composed of stainless steel, is located proximate to upper end plate 32 and is moveable to open cooperatively with the downward movement of plunger 19. Shutter 31 is positioned by annular surround 30. Shutter 31 is spring biased to open when the pressure on the inside of the shutter in upper vacuum chamber 11 reaches the pressure outside the shutter, which generally is atmospheric pressure. The opening of shutter 31 activates electromagnetic switches 33 or other switch means. One electromagnetic switch activates downward movement of plunger 19, and the tissue sample is slammed or plunged against the cryogenic surface 38. The second electromagnetic switch shuts off dry helium gas input into the upper vacuum chamber. Although electromagnetic switches are shown in the preferred embodiment, it is contemplated under the present invention that other means such as electropneumatic means or hydraulic means may be used to activate downward movement of the plunger and control dry helium gas input to the upper vacuum chamber. Upper vacuum chamber 11 is further provided with radiation shields 40 enclosed within side walls 39 of the upper vacuum chamber to reduce the heat transfered by radiation to the upper vacuum chamber.

The cryogenic surface 38 located in upper vacuum chamber 11 may be composed of copper, gold, silver, diamond or sapphire or combinations thereof or other suitable means having high heat conductivity at low temperatures and providing a mirror-finished flat smooth surface for contact with tissue samples. The preferred cryogenic surface is copper with a sapphire outer portion. The cryogenic surface is the outer layer over a substrate of materials positioned directly adjacent to thermal break 12. Attached to the cryogenic surface is heating element or cartridge 42, which is provided for heating the cryogenic surface in order to remove condensation and clean the cryogenic surface between successive tissue samples. The heating element or cartridge is connected to electrical connector 44 and a heater input preferably having a temperature regulator. The heating element or cartridge thus enables regeneration of the cryogenic surface for rapid turnover of samples. Attached to heating element or cartridge 42 is upper end plate 45 of the thermal break, which preferably is composed of copper or other suitable material having high heat conductivity at low temperatures. Thermal damper 41 may be positioned between cryogenic surface 38 and heating element 42, if it is desired to reduce temperature fluctuations. The cryogenic surface 38, heating element or cartridge 42, and thermal damper 41 are removably fixed to upper end plate 45; and in the preferred embodiment are removable as a unit through the shutter opening, by loosening and removing screws 40 and 40A. Thermocouple 43 and electrical connector 44 are functionally connected to the cryogenic surface for sensing the temperature of the surface, for example, by use of a silicon dioxide resistor or a germanium chip. Optionally, mannometer thermometer 71 may be used to sense the temperature of the cryogenic surface.

Thermal break 12 includes side walls 46 preferably composed of stainless steel and ceramic walls 48 bonded to the wall separating the upper and lower vacuum chambers. Upper end plate 45 and lower end plate 49 preferably composed of copper or other highly conductive material at low temperature are provided at each end of thermal break 12. Vanes 47, comprised of copper or other suitable material having high heat conductivity at low temperature, extend between upper end plate 45 and lower end plate 49 of the thermal break. The vanes connected to the upper and lower end plates, respectively, are not interconnected, but improve the efficiency for removing heat from the cryogenic surface to nearly 70% when dry helium gas is reintroduced into the thermal break and the cryogenic surface is cooled. The vanes as used in the thermal break increase the efficiency of cooling (between lower end plate 49 and upper end plate 45 of the thermal break) by convection rather than by conduction.

The lower vacuum chamber 13 includes side walls 70, radiation shields 72 within the side walls to reduce the radiant heat transfer to the lower vacuum chamber, and lower end plate 77. In the preferred embodiment, a cryopump or multiple stage refrigerator operating on the Gifford-McMahon principle and using gaseous helium as the coolant is utilized. Preferably, the refrigerator second stage 73 is enclosed within lower vacuum chamber 13. The refrigerator second stage 73 is further connected to refrigerator first stage 76 enclosed by side walls 74 and upper end plate 75.

An external vacuum pump is utilized to create a vacuum in the upper and lower vacuum chambers and thermal break. The vacuum pump is connected via upper chamber vacuum inlet 51 and upper chamber vacuum valve 52, thermal break vacuum inlet 53 and thermal break vacuum valve 54, and lower chamber vacuum inlet 55 and lower chamber vacuum valve 56. The vacuum pump preferably is a vibration isolated turbo molecular vacuum pump or vane pump or equivalent device for creating a vacuum of at least $10^{-3}$ Mbar in the upper vacuum chamber and lower vacuum chamber. The vacuum pump employed can be any of a variety of commercially available vacuum pumping apparatus. It is essential that the pump, whether or not it is a turbomolecular pump, yield a hydrocarbon-free vacuum. However, the helium cryopump or multiple stage refrigerator is used to further reduce the pressure in the upper and lower vacuum chambers to preferably about $10^{-8}$ Mbar.

The upper vacuum chamber is provided with upper chamber dry helium inlet 58 and upper chamber dry helium inlet valve 59. Additionally, thermal break 12 is provided with thermal break dry helium inlet 60 and thermal break dry helium inlet valve 61. An external dry helium source with controls is used to regulate the supply of dry helium to the upper vacuum chamber and thermal break.

The operation of the present invention in the preferred embodiment is set forth below. Initially upper chamber vacuum valve 52 and lower chamber vacuum valve 56 are opened. Thermal break vacuum valve 54 is closed. The upper and lower vacuum chambers are evacuated with an external vacuum pump system to reach a vacuum of $10^{-3}$ Mbar. The vacuum in the upper vacuum chamber helps to prevent undesirable hydrocarbon deposits on the cryogenic surface 38 and undesirable condensation on the cryogenic surface while it is cooled. An external vacuum pump is used to create a vacuum of about $1 \times 10^{-3}$ Mbar surrounding the cryopump or multiple stage refrigerator. The external vacuum pump system used helps to prevent condensation in the lower chamber and improve the cooling capability of the cryopump or multiple stage refrigerator. To achieve a hydrocarbon-free vacuum in the upper chamber, however, a lower vacuum pressure is desired. Accordingly, the helium cryopump is utilized to reach a vacuum of approximately $1 \times, 10^{-8}$ Mbar. The external dry helium source also is activiated to fill thermal break 12 with dry helium gas or other thermally conductive gas.

In the preferred embodiment, the cooling of the cryogenic surface is achieved by a helium cryopump or multiple stage refrigerator using a closed helium gas cycle operating on the Gifford-McMahon principle. The Gifford-McMahon refrigerator is a modification of the Stirling-cycle refrigerator. For lower temperatures of between $-270°$ C. and $-200°$ C. as required by the present invention, a refrigerator having two or more stages is preferred. Although the preferred embodiment discloses the use of a two-stage refrigerator operating on the Gifford-McMahon principle, it will be understood that other cryopumps or refrigerators are within the scope of the present invention. In the preferred embodiment, the second stage of the refrigerator is enclosed within the lower vacuum chamber 13, and controllably cools the cryogenic surface when the thermal break is filled with dry helium gas.

Once temperature of the cryogenic surface has reached equilibrium, preferably between $-270°$ C. and $-200°$ C., upper chamber vacuum valve 52 is closed. At this time both the upper and lower chambers are at a vacuum of preferably about $1 \times 10^{-8}$ Mbar. A tissue sample or specimen is then mounted on sample holder 24. According to the present invention, more than one tissue sample may be slammed or plunged against the cryogenic surface at one time, depending on the particular sample holder utilized and the sample turnover desired.

In the preferred embodiment, prior to slamming the sample against the cryogenic surface, upper vacuum chamber dry helium inlet valve 59 is opened to allow dry helium gas at room temperature to enter the upper vacuum chamber and raise the pressure inside the upper vacuum chamber to atmospheric pressure. The use of dry helium gas at room temperature prevents pre-cooling of the specimen during movement towards cryogenic surface 38. Helium gas is a non-condensable gas and thus will not condense on the cryogenic surface. It should be understood that any other noncondensable gas may be used, preferably at room temperature, to raise the pressure inside upper vacuum chamber without undesirable condensation on the cryogenic surface or precooling the tissue sample. When the upper vacuum chamber reaches atmospheric pressure, wherein the pressure inside of shutter 31 equals that outside of the shutter, a spring moves the shutter to an open position and triggers a switch to activate downward movement of the plunger and tissue sample towards the cryogenic surface. The shutter also triggers a switch to close the upper chamber dry helium inlet valve 59. The switches may be electromagnetically or electropneumatically activated or operated by other means triggered by the opening of shutter 31. The shutter spring is biased to open when the pressure inside the upper vacuum chamber reaches the outside pressure, generally at atmospheric pressure. The plunger descends into the upper vacuum chamber and the tissue sample is slammed or plunged against the cryogenic surface. In the present invention, the cooling rate of the tissue sample or specimen is in excess of 10,000° C./second to a depth of 30–70 microns in the sample, thereby achieving amorphous or microcrystalline ice to this depth. At the time of application of the sample, the cryogenic surface preferably is at a temperature of −270° C. to −200° C.

After the sample is plunged or slammed against the cryogenic surface, the sample holder is removed from the sample delivery assembly and placed a in liquid nitrogen bath at −196° C. Optionally, at this point the upper vacuum chamber is filled with liquid nitrogen and the sample is removed from the upper vacuum chamber while continuously enclosed in the liquid nitrogen at −196° C. for storage. The use of liquid nitrogen in the chamber reduces the handling of the sample between the chamber and a liquid nitrogen Dewar for storage and maintains the cool temperature of the sample after it is removed from the sample holder.

The thermal break 12 is then evacuated by an external vacuum pump system to reach a vacuum of preferably about $1 \times 10^{-3}$ Mbar when thermal break vacuum valve 54 is opened. The vacuum in the thermal break functionally separates the cryogenic surface from the cooling of the cryopump. Heating element 42 is then activated to raise the temperature of the cryogenic surface. It is preferred that the shutter be closed during heating of the surface to reduce the amount of condensation and/or contaminants deposited on the cryogenic surface and it is most preferred that the shutter be biased closed immediately upon return or recoil of the plunger to its resting position so that the cryogenic surface is maintained under vacuum during heating. When the cryogenic surface reaches the desired temperature, preferably room temperature, the cryogenic surface may be cleaned, preferably with acetone and freon. By functionally separating the cryogenic surface from the cryopump or multiple stage refrigerator, it is possible to regenerate or heat and clean the cryogenic surface at room temperature, then recool the cryogenic surface without lengthy delay. In the past, the turnaround time between each sequential tissue sample has been several hours or more, due to the time for heating the block and reactivating the entire cooling system. In the present invention, the turnaround regeneration time is reduced to between 10 and 15 minutes.

After the cryogenic surface is cleaned, shutter 31 is closed and the upper vacuum chamber is reevacuated by by the external vacuum pump to preferably about $1 \times 10^{-3}$ MBar when upper chamber vacuum valve 52 is opened. When a vacuum of $1 \times 10^{-3}$ Mbar is obtained in the upper vacuum chamber, heating element 42 is switched off and thermal break vacuum valve 54 is closed. The upper chamber and lower chamber are reconnected to achieve the hydrocarbon-free ultravacuum in the upper chamber. Dry helium gas is reintroduced into the thermal break via thermal break dry helium inlet 60 and thermal break dry helium inlet valve 61. This restores the functional relationship of the cryopump or multiple stage refrigerator to cool the cryogenic surface to the desired temperature. The cryopump then cools the block and obtain a vacuum of preferably about $1 \times 10^{-8}$ Mbar in the upper and lower chambers and the cycle is repeated.

According to the present invention it is possible to vitrify a large number of tissue samples sequentially after regenerating the cryogenic surface between each sample. The cryogenic surface is heated to preferably room temperature, cleaned and rapidly recooled between each tissue sample. During cooling, the cryogenic surface is in an ultra-high hydrocarbon-free vacuum. Condensation on the cryogenic surface and/or contamination of the cryogenic surface does not occur prior to application of the tissue sample. Precooling of the sample and condensation on the cryogenic surface is prevented by introducing room temperature dry helium gas, or other non-condensable gas at room temperature, into the upper vacuum chamber for controlling the opening of the shutter sealing the upper chamber and slamming or plunging the tissue sample against the cryogenic surface.

The present invention employs a recirculating liquid helium cryopump, shown in the preferred embodiment as a two-stage refrigerator operating on the Gifford-McMahon principle to cool the cryogenic surface rather than an external nonreusable cryogen source such as liquid helium or liquid nitrogen, as used in the prior art. Helium pumps manufactured by Leybold-Heraeus Vacuum Products provide examples of the cryopumps used in the present invention. The present invention also eliminates problems of vibration to the cryogenic surface due to movement of liquid helium and helium gas proximate to the surface before slamming. Additionally, the present invention incorporates a thermal break as a modification of a helium cryopump, and incorporates a heating unit for rapid regeneration of the cryogenic surface. These features make cryopreparation considerably more economically productive because tissue samples may be processed sequentially while maintaining the cryogenic surface free from contamination.

Although the preferred embodiment of this invention has been described hereinabove in some detail, it should be appreciated that a variety of embodiments will be readily available to a person designing such cryopreparation apparatus for a specific end use. The description of the apparatus of this invention is not intended to be limiting on this invention, but is merely illustrative of the preferred embodiment of this invention. Other apparatus and components which incorporate modifications or changes to that which has been described herein are equally included within this application.

What is claimed:

1. Cryopreparation apparatus for the ultrarapid cooling of one or more biological samples without the formation of resolvable ice crystals in at least a portion of said one or more biological samples comprising:
    (a) a housing, said housing enclosing a flat, mirror-finished, cryogenic surface, said cryogenic surface characterized by high heat conductivity at low temperatures;
    (b) a sample delivery assembly, said assembly including a plunger mounted in a support structure, said plunger being moveable into and out of said housing, said support structure being cooperatively engaged to said housing said plunger being cooperatively aligned with said cryogenic surface such that said plunger's path of travel permits said plunger and one or more biological samples mounted thereon to penetrate into said housing and into a mated position with said cryogenic surface;

(c) an intrinsic cryogenic source functionally attached to said cryogenic surface;

(d) a regeneration system functionally attached to said cryogenic surface for removing contaminants from said cryogenic surface; and (e) a thermal switch controllably insulating said cryogenic surface from said intrinsic cryogenic source.

2. The cryopreparation apparatus of claim 1 wherein said thermal switch includes first and second copper end plates, said first copper end plate being fixedly attached proximate to said cryogenic surface and said second copper end plate being fixedly attached to said intrinsic cryogenic source.

3. The cryopreparation apparatus of claim 1 wherein said thermal switch further includes sidewalls made from a combination of ceramic material and stainless steel.

4. The cryopreparation apparatus of claim 1 wherein said thermal switch further includes copper vanes.

5. The cryopreparation apparatus of claim 1 wherein said thermal switch further includes inlet and outlet means for an inert gas.

6. The cryopreparation apparatus of claim 1 wherein said thermal switch is functionally adapted to maintain a vacuum.

7. Cryopreparation apparatus for the ultra-rapid cooling of one or more biological samples without the formation of resolvable ice crystals in at least a portion of said one or more biological samples comprising:

(a) a first chamber, said first chamber housing a flat, mirror-finished, cryogenic surface, said cryogenic surface characterized by high heat conductivity at low temperatures;

(b) a sample delivery assembly including a plunger mounted in a support structure, said plunger being moveable into and out of said first chamber, said sample delivery assembly further including a sample holder, said sample holder being characterized by a construction which minimizes compression and bounce upon contact with said cryogenic surface;

(c) said plunger and said sample holder being cooperatively aligned with said cryogenic surface such that the path of travel of said plunger and said sample holder permits said plunger and said sample holder and the one or more biological samples mounted in said sample holder to penetrate into said first chamber and into a mated position with said cryogenic surface without substantial atmospheric contamination of said cryogenic surface;

(d) an intrinsic cryogenic source functionally attached to said cryogenic surface;

(e) a second chamber housing said intrinsic cryogenic source, said second housing functioning as a vacuum chamber which includes a thermal switch to controllably insulate said cryogenic surface from said intrinsic cryogenic source during regeneration prior to establishing cryopreparation conditions in said first chamber; and (f) a regeneration system functionally attached to said cryogenic surface for removing contaminates from said cryogenic surface.

8. The cryopreparation apparatus of claim 7 wherein said first chamber further includes temperature sensing means functionally attached to said cryogenic surface.

9. The cryopreparation apparatus of claim 7 wherein said first chamber further includes a radiation shield.

10. The cryopreparation apparatus of claim 7 wherein said first chamber further includes inlet and outlet means for an inert gas.

11. The cryopreparation apparatus of claim 7 wherein said cryogenic surface is made from material selected from the group consisting of: copper, gold, silver, sapphire, diamond or combinations thereof.

12. The cryopreparation apparatus of claim 7 wherein said cryogenic surface comprises a major portion of gold, a minor portion of silver, and is copper plated.

13. The cryopreparation apparatus of claim 7 wherein said regeneration system comprises a heater.

14. The cryopreparation apparatus of claim 7 wherein said sample delivery assembly is electromagnetically actuated.

15. The cryopreparation apparatus of claim 7 wherein said sample delivery assembly further includes a moveable shutter controlling access of said plunger into said first chamber.

16. The cryopreparation apparatus of claim 7 wherein said sample holder includes a magnetic disc; a foam rubber cushion; a brass plate; and mounting means for said biological tissue.

17. The cryopreparation apparatus of claim 7 wherein said second chamber includes a radiation shield.

18. The cryopreparation apparatus of claim 7 wherein said second chamber includes inlet and outlet means for an inert gas.

19. The cryopreparation apparatus of claim 7 wherein said thermal switch is functionally adapted to maintain a vacuum.

20. The cryopreparation apparatus of claim 7 wherein said second chamber further includes temperature sensing means functionally attached to said intrinsic cryogenic source.

21. The cryopreparation apparatus of claim 7 wherein said thermal switch includes first and second copper end plates, said first copper end plate being fixedly attached to said cryogenic surface and said second copper end plate being fixedly attached to said intrinsic cryogenic source.

22. The cryopreparation apparatus of claim 7 wherein said thermal switch further includes sidewalls made from a combination of ceramic material and stainless steel.

23. The cryopreparation apparatus of claim 7 wherein said thermal switch further includes copper vanes.

24. The cryopreparation apparatus of claim 7 wherein said thermal switch further includes inlet and outlet means for thermally conducting gas.

25. The cryoprepartion apparatus of claim 7 wherein said cryogenic surface is removable and replaceable as a unit from within said second chamber.

26. The cryopreparation apparatus of claim 7 wherein said housing includes inlet and outlet means for liquid nitrogen.

27. The cryopreparation apparatus according to claim 7 wherein said cryogenic surface comprises a major part of copper and a minor part of sapphire.

28. The cryopreparation apparatus of claim 7 wherein said intrinsic cryogenic source comprises a helium cryopump for recirculating gaseous helium and controllably cooling said cryogenic surface.

29. The cryopreparation apparatus of claim 28 wherein said helium cryopump comprises a two stage refrigerator operating on the Gifford-McMahon principle.

30. A portable cryopreparation apparatus for the ultrarapid cooling of one or more biological samples without the formation of resolvable ice crystals in at least a portion of said one or more biological samples comprising:
- (a) a first vacuum chamber housing a cryogenic surface, said cryogenic surface being planar and having a mirror finish, said cryogenic surface being further characterized by high heat conductivity at low temperatures, said first vacuum chamber including means for controllably depressurizing the interior of said first chamber;
- (b) a sample delivery assembly including (i) a moveable plunger mounted in a support structure, said support structure being fixedly attached to said first vacuum chamber, (ii) a sample holder detachably mounted to one end of said plunger, said sample holder being characterized by a construction that minimizes compression and bounce when said one or more samples are brought into sudden, intimate contact with said cryogenic surface, and (iii) a moveable shutter controlling access of said plunger into said first vacuum chamber, said plunger and said sample holder being characterized by a linear path of travel that permits said plunger and said sample holder to penetrate through a space created by withdrawal of said moveable shutter into said first vacuum chamber and into mated position with said cryogenic surface;
- (c) a second vacuum chamber fixedly attached to said first vacuum chamber, said second vacuum chamber housing an intrinsic cryogenic source and a thermal switch, said thermal switch being functionally effective to insulate said cryogenic surface from said intrinsic cryogenic source during regeneration prior to establishing cryopreparation conditions in said first chamber; and
- (d) a heater mounted adjacent said cryogenic surface, said heater functioning to remove contaminants from said cryogenic surface.

31. Cryopreparation apparatus for the ultra-rapid cooling of one or more biological samples without the formation of resolvable ice crystals in at least a portion of said one or more biological sampels comprising:
- (a) a housing, said housing enclosing a flat, mirror-finished, cryogenic surface, said cryogenic surface characterized by high heat conductivity at low temperatures;
- (b) a sample delivery assembly, said assembly including a plunger mounted in a support structure, said plunger being moveable into and out of said housing, said support structure being cooperatively engaged to said housing said plunger being cooperatively aligned with said cryogenic surface such that said plunger's path of travel permits said plunger and one or more biological samples mounted thereon to penetrate into said housing and into a mated position with said cryogenic surface, wherein said sample delivery assembly further includes a sample holder, said sample holder being characterized by a construction which minimizes compression and bounce upon contact with said cryogenic surface, and wherein said samples holder includes a magnetic disc, a foam rubber cushion, a brass plate, and a mounting means for said biological samples;
- (c) an intrinsic cryogenic source functionally attached to said cryogenic surface; and
- (d) a regeneration system functionally attached to said cryogenic surface for removing contaminants from said cryogenic surface.

32. Cryopreparation apparatus for the ultra-rapid cooling of one or more biological samples without the formation of resolvable ice cyrstals in at least a portion of said one or more biological samples comprising:
- (a) a housing, said housing enclosing a flat, mirror-finished, cryogenic surface, said cryogenic surface characterized by high heat conductivity at low temperatures wherein said housing includes a first chamber and a second chamber, said first chamber enclosing said cryogenic surface and said second chamber enclosing said intrinsic cryogenic source, said first and second chambers being fixed attached to one another, and wherein said second chamber is a vacuum chamber which includes a thermal switch which functions to controllably insulate said cryogenic surface from said intrinsic cryogenic source during regeneration prior to establishing cryopreparation conditions in said first chamber;
- (b) a sample delivery assembly, said assembly including a plunger mounted in a support structure, said plunger being moveable into and out of said housing, said support structure being cooperatively engaged to said housing said plunger being cooperatively aligned with said cryogenic surface such that said plunger's path of travel permits said plunger and one or more biological samples mounted thereon to penetrate into said housing and into a mated position with said cryogenic surface;
- (c) an intrinsic cryogenic source functionally attached to said cryogenic surface; and
- (d) a regeneration system functionally attached to said cryogenic surface for removing contaminants from said cryogenic surface.

33. Cryopreparation apparatus for the ultra-rapid cooling of one or more biological samples without the formation of resolvable ice crystals in at least a portion of said one or more biological samples comprising:
- (a) a housing, said housing enclosing a flat, mirror-finished, cryogenic surface, said cryogenic surface characterized by high heat conductivity at low temperatures, wherein said housing includes a first chamber and a second chamber, said first chamber enclosing said cryogenic surface and said second chamber enclosing said intrinsic cryogenic source, said first and second chambers being fixed attached to one another, and wherein said second chamber includes a thermal switch which is a vacuum chamber and includes means for cooling by repressurization with dry helium gas;
- (b) a sample delivery assembly, said assembly including a plunger mounted in a support structure, said plunger being moveable into and out of said housing, said support structure being cooperatively engaged to said housing said plunger being cooperatively aligned with said cryogenic surface such that said plunger's path of travel permits said plunger and one or more biological samples mounted thereon to penetrate into said housing and into a mated position with said cryogenic surface;
- (c) an intrinsic cryogenic source functionally attached to said cryogenic surface; and
- (d) a regeneration system functionally attached to said cryogenic surface for removing contaminants from said cryogenic surface.

* * * * *